United States Patent [19]

Bellina et al.

[11] 4,148,918
[45] Apr. 10, 1979

[54] SUBSTITUTED 2-HIGHER ALKYL-3-HYDROXY-1,4-NAPHTHOQUINONE CARBOXYLIC ACID ESTERS AND THEIR USE AS MITICIDES

[75] Inventors: Russell F. Bellina, Wilmington; Dennis L. Fost, Newark, both of Del.

[73] Assignee: E. I. Du Pont de Nemours and Company, Wilmington, Del.

[21] Appl. No.: 929,802

[22] Filed: Jul. 31, 1978

Related U.S. Application Data

[60] Division of Ser. No. 841,453, Oct. 12, 1977, Pat. No. 4,115,584, which is a division of Ser. No. 671,044, Mar. 29, 1976, Pat. No. 4,070,481, which is a continuation-in-part of Ser. No. 613,553, Sep. 15, 1975, Pat. No. 4,055,661, which is a continuation-in-part of Ser. No. 531,483, Dec. 11, 1974, abandoned, which is a continuation-in-part of Ser. No. 494,294, Aug. 2, 1974, abandoned, Continuation of Ser. No. 468,692, May 10, 1974, abandoned.

[51] Int. Cl.$^2$ .................. A01N 9/00; A01N 9/24; C07C 69/96
[52] U.S. Cl. ................ 424/314; 260/396 R; 424/312
[58] Field of Search ................ 424/312, 314; 260/396 R

[56] References Cited

U.S. PATENT DOCUMENTS

| 2,553,647 | 5/1951 | Fieser et al. | 260/396 |
| 2,553,648 | 5/1951 | Fieser et al. | 260/396 |
| 2,572,946 | 10/1951 | Paulshock | 424/331 |

OTHER PUBLICATIONS

J. Econ. Ent., 1962, 55, pp. 737–743, Chapman et al.
Nakanishi et al., J.A.C.S., 1952, pp. 3910–3915.

Primary Examiner—Allen J. Robinson

[57] ABSTRACT

This invention relates to novel compounds which are represented by the following formula:

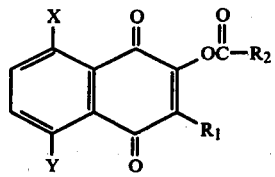

wherein
$R_1$ is alkyl of 8–14 carbon atoms either branched, cyclic or straight chain; and
$R_2$ is alkyl of 1–17 carbon atoms either branched or straight chain, alkenyl of 2–17 carbon atoms, cycloalkyl of 3–6 carbon atoms, alkoxy of 1–4 carbon atoms, $-CH_2OCH_3$, $-CH_2OCH_2CH_3$ or $-CH=CH-CO_2H$;
X is hydrogen, fluorine, chlorine, bromine, methyl or methoxy; and
Y is hydrogen, fluorine, chlorine, bromine, methyl or methoxy;
provided that at least one of X and Y is other than hydrogen. The novel compounds possess miticidal and aphicidal activity.

21 Claims, No Drawings

SUBSTITUTED 2-HIGHER ALKYL-3-HYDROXY-1,4-NAPHTHOQUINONE CARBOXYLIC ACID ESTERS AND THEIR USE AS MITICIDES

CROSS-REFERENCE TO RELATED APPLICATIONS

This application is a division of our copending application Ser. No. 841,453, filed Oct. 12, 1977 (now U.S. Pat. No. 4,115,584), which in turn is a division of our copending application Ser. No. 671,044, filed Mar. 29, 1976 (now U.S. Pat. No. 4,070,481), which in turn is a continuation-in-part of application Ser. No. 613,553, filed Sept. 15, 1975 (now U.S. Pat. No. 4,055,661), which in turn is a continuation-in-part of application Ser. No. 531,483, filed Dec. 11, 1974 (now abandoned), which in turn is a continuation-in-part of application Ser. No. 494,294, filed Aug. 2, 1974 (now abandoned), which in turn is a continuation-in-part of application Ser. No. 468,692, filed May 10, 1974 (now abandoned).

BACKGROUND OF THE INVENTION

This invention relates to miticidal and aphicidal compounds which are 2-higher alkyl-3-hydroxy-1,4-naphthoquinone carboxylic acid esters.

U.S. Pat. Nos. 2,553,647 and 2,553,648 disclose broadly 2-alkyl-3-hydroxy-1,4-naphthoquinone carboxylic acids and their corresponding ester derivatives. These compounds are described as having antagonistic action against organisms which cause malarial infections.

U.S. Pat. No. 2,572,946 discloses the use of non-acylated compounds as miticides; it contains no teaching of acylated compounds.

Nakanishi et al. JACS 1952, 3910–3915 discloses the n-undecyl analog of 2-alkyl-3-hydroxy-1,4-naphthoquinone. No use for the composition is disclosed.

SUMMARY OF THE INVENTION

This invention is a class of novel aphicidal and miticidal compounds of the formula:

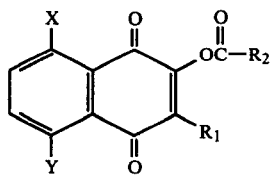

wherein
$R_1$ is alkyl of 8–14 carbon atoms which are branched, cyclic, or straight chain;
$R_2$ is alkyl of 1–17 carbon atoms either branched or straight chain, alkenyl of 2–17 carbon atoms, cycloalkyl of 3–6 carbon atoms, alkoxy of 1–4 carbon atoms, $-CH_2OCH_3$, $-CH_2OCH_2CH_3$ or $-CH=CH-CO_2H$;
X is hydrogen, fluorine, chlorine, bromine, methyl or methoxy; and
Y is hydrogen, fluorine, chlorine, bromine, methyl or methoxy;
provided that at least one of X and Y is other than hydrogen.

The compounds of Formula I are miticides and aphicides. This invention includes a method of protecting plants from aphids and mites by bringing an effective amount of such compounds into contact with such mites or aphids.

The invention also includes miticidal and aphicidal compositions which consist essentially of at least one compound of Formula I as active ingredient, an inert diluent and/or a surfactant.

Preferred for their ease of synthesis and/or higher biological activity are those compounds of Formula I where, independently:
(a) Either X or Y is hydrogen;
(b) $R_1$ is alkyl of 11–14 carbon atoms either branched or straight-chain; or
(c) $R_2$ is alkyl of 1–6 carbon atoms, alkenyl of 2 or 3 carbon atoms, methoxy or ethoxy.

More preferred for higher biological activity are those compounds of Formula I in which $R_1$ is a straight chain alkyl of 11–14 carbon atoms, Y is hydrogen, and $R_2$ is methyl or ethyl.

Specifically preferred is the compound: 3-acetoxy-5-chloro-2-dodecyl-1,4-naphthoquinone.

In a specific embodiment of the instant invention, the compounds of the instant invention are applied in admixture with a superior oil, preferably a minor amount of superior oil, e.g., less than 5% by weight but more than 1% by weight. The resulting miticidal activity is greater than the additive results. Superior oils are discussed in Chapman et al., *Selection of a Plant Spray Oil Combining Full Pesticidal Efficiency with Minimum Plant Injury Hazards*, Jour. Econ. Ent., 1962, 55:737–43, the disclosure of which is herein incorporated by reference. The resulting mixture of the compound and the superior oil is novel.

DESCRIPTION OF THE INVENTION

Synthesis

The compounds of this invention can be prepared either (a) from the appropriately-substituted naphthol by the method taught in published German Offenlegungschrift #2,520,739, (11/9/75), or (b) from the appropriate 4-phenyl-3-oxobutanoic ester as taught by Fieser, et al., U.S. Pat. No. 2,553,647:

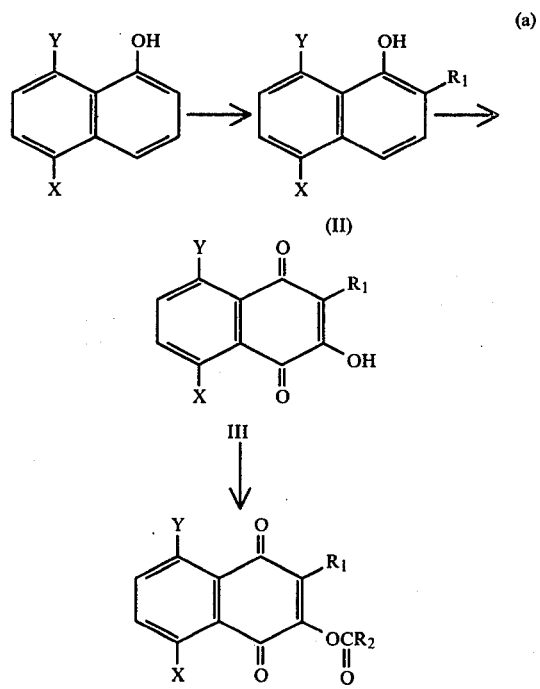

-continued (b) 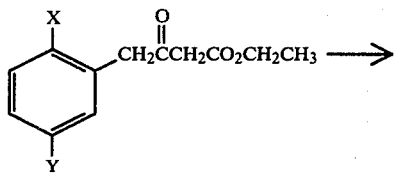

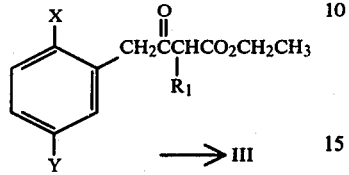 → III

The final step in the synthesis may be accomplished by treating the corresponding 2-alkyl-3-hydroxy-1,4-naphthoquinone with the appropriate acid chloride or anhydride in the presence of at least an equivalent of an amine such as pyridine or triethylamine, or by treating the salt of the 2-alkyl-3-hydroxy-1,4-naphthoquinone with the appropriate acid chloride or anhydride in an inert solvent. The following examples are given to illustrate the above-described processes.

EXAMPLE 1

Preparation of Ethyl 2-Acetyl-4-(2-Methylphenyl)-3-oxobutanoate

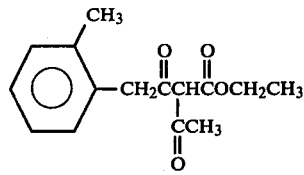

This material was prepared according to the procedure of M. Viscontini and N. Merckling, *Helvetica Chimica Acta*, 35, 2280 (1952). To 2.65 parts of magnesium turnings was added 15 parts absolute ethanol at room temperature and 0.5 parts of carbon tetrachloride. As soon as the initial reaction subsides 100 parts of dry ether was added. The mixture was stirred without cooling until the reaction ceased, then 19.6 parts of ethyl 3-oxobutanoate in 20 parts of dry ether was added with ice cooling and good stirring. After the resulting precipitate dissolved, the solution was cooled in an ice-salt bath and 16 parts of 2-methylphenylacetyl chloride was slowly added. The mixture was allowed to stand overnight at room temperature and then combined with ice and sulfuric acid. The ether layer was separated, washed with water, dried over sodium sulfate and stripped to give ethyl 2-acetyl-4-(2-methylphenyl)-3-oxobutanoate as a crude oil.

EXAMPLE 2

Preparation of Ethyl 4-(2-Methylphenyl)-3-oxobutanoate

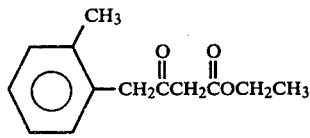

Following the method of Hunsdiecker [*Berichte*, 75, 454 (1942)], 26 parts of ethyl 2-acetyl-4-(2-methylphenyl)-3-oxobutanoate was stirred for 10 hours at room temperature with 100 parts ethanol and 6.8 parts of sodium ethoxide. The mixture was diluted with water and extracted with ether. The solvent was then evaporated to give ethyl 4-(2-methylphenyl)-3-oxobutanoate.

EXAMPLE 3

Preparation of Ethyl 2-[(2-Methylphenyl)acetyl]tetradecanoate

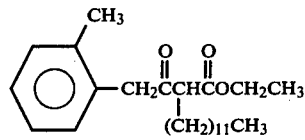

Three parts of ethyl 4-(2-methylphenyl)-3-oxobutanoate, 1 part of sodium methoxide, 4.6 parts of 1-bromododecane, 0.5 parts of potassium iodide and 50 parts of absolute ethanol were refluxed together for 4 hours and then stirred 18 hours at room temperature. The mixture was evaporated to a small volume, diluted with 100 parts water and extracted with ether. The ether extract was washed with saturated sodium bicarbonate, saturated sodium chloride solution and dried over magnesium sulfate. Evaporation of the ether gave 6 parts of crude ethyl 2-[(2-methylphenyl)acetyl]tetradecanoate as an oil which was not further purified.

EXAMPLE 4

Preparation of 2-Dodecyl-3-hydroxy-5-methyl-1,4-naphthoquinone

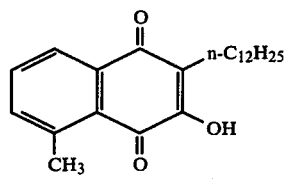

Four parts of crude ethyl 2-[(2-methylphenyl)acetyl]-tetradecanoate obtained in Example 3 was combined with 12 parts of cold concentrated sulfuric acid and stirred at room temperature for 66 hours. The mixture was poured into ice water and made slightly basic by the addition of 50% aqueous sodium hydroxide. Enough ethanol was added to dissolve the organic matter and air was then bubbled through the solution for 3 hours. The resulting solution was extracted with 100 parts petroleum ether (twice), acidified with hydrochloric acid and re-extracted with diethylether. The ether extract was washed with saturated sodium chloride, dried over magnesium sulfate and evaporated. The residue was taken up in acetonitrile and filtered. The filtrate was evaporated to dryness and the residue triturated with petroleum ether to give 0.2 g of 2-dodecyl-3-hydroxy-5-methyl-1,4-napthoquinone, m.p. 92°–93° C.

EXAMPLE 5

Preparation of
3-Acetoxy-2-dodecyl-5-methyl-1,4-naphthoquinone

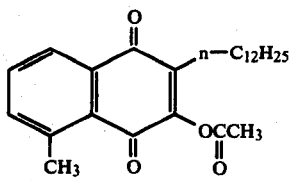

3.8 Parts of 2-dodecyl-3-hydroxy-5-methyl-1,4-naphthoquinone, 8 parts of acetic anhydride and 32 parts of pyridine were stirred at room temperature for 16 hours. The resulting mixture was evaporated under reduced pressure to remove the pyridine. The residue was recrystallized from methanol to give 2.5 parts of 3-acetoxy-2-dodecyl-5-methyl-1,4-naphthoquinone, m.p. 69°–75° C.

EXAMPLE 6

Preparation of
1-(5-Chloro-1-hydroxynaphthalen-2-yl)-1-dodecanone

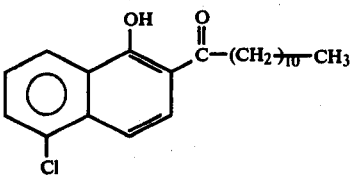

A mixture of 16.6 parts of 5-chloro-1-naphthalenol [Erdmann and Kirchoff, *Liebig's* Ann., 247, 372 (1888)] 19.2 parts of dodecanoic acid and 132 parts of boron trifluoride ether complex (48% $BF_3$) was stirred under nitrogen on a steam bath for 6 hours. Water (114 parts) was added and ether distilled off by further heating. The resulting mixture was cooled in ice and a tan solid was filtered and recrystallized from ethanol to give 18 parts of yellow 1-(5-chloro-1-hydroxynaphthalen-2-yl)-1-dodecanone, m.p. 86°–87° C.

EXAMPLE 7

Preparation of 5-Chloro-2-dodecyl-1-naphthalenol

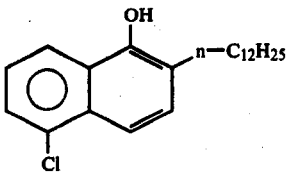

A solution of 17.4 parts of 1-(5-chloro-1-hydroxynaphthalen-2-yl)-1-dodecanone and 107 parts of 37% hydrochloric acid in 2.5 parts of ethanol was contacted with stirring at reflux during 26 hours, with 40 parts of zinc dust which has been amalgamated by treatment with 3 parts of mercuric chloride and 53 parts of 2.1% hydrochloric acid followed by washing with ethanol. The zinc amalgam was added in small portions throughout the reaction period. Upon cooling, a solid separated. After dissolution of this solid in ethanol, zinc amalgam was filtered, and cooling gave 0.5 parts of starting material which was filtered. Concentration of the filtrate, purification by recrystallization from ethanol, and column chromatography on silica gel using 1-chlorobutane as eluent gave 12 parts of 5-chloro-2-dodecyl-1-naphthalenol, m.p. 68°–70° C.

EXAMPLE 8

Preparation of 5-Chloro-2-dodecyl-1,4-naphthoquinone

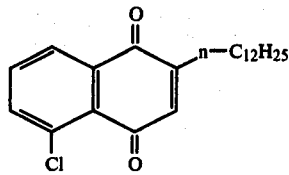

A mixture of 5.4 parts of 5-chloro-2-dodecyl-1-naphthalenol, 18 parts of 96% sulfuric acid, 71.5 parts of glacial acetic acid, and 29 parts of water was stirred at 70° C. and 8.85 parts of cold 30% hydrogen peroxide was added dropwise over 8 hours. Stirring at 70° C. was continued for another 17 hours. The mixture was cooled and an orange solid taken up in methylene chloride, and the extract washed with water, dried and stripped. The resulting tan solid was purified by column chromatography from 1-chlorotutane on silica gel to give 2 parts of 5-chloro-2-dodecyl-1,4-naphthoquinone, m.p. 57.5°–58.5° C.

EXAMPLE 9

Preparation of
5-Chloro-2-dodecyl-3-hydroxy-1,4-naphthoquinone

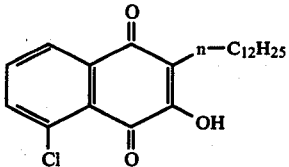

A mixture of 1.7 parts of 5-chloro-2-dodecyl-1,4-naphthoquinone, 25 parts ethanol, 0.626 parts anhydrous sodium carbonate and 6.3 parts water was contacted with 1.13 parts of 30% hydrogen peroxide at 32° C. and then refluxed for 10 minutes. The resulting mixture was then cooled to 50° C. and a solution of 1.56 parts of potassium hydroxide in 49.5 parts of ethanol was added to it. The resulting deep red mixture was then heated to 50° C. over 25 minutes and the temperature held there for 45 minutes. After cooling to 10° C. the mixture was then contacted with 251 parts of 2.72% hydrochloric acid. The resulting yellow crystals were filtered, dried and purified by column chromatography on silica gel using 1-chlorobutane as eluent. Solvent removal gave 1.4 parts of 5-chloro-2-dodecyl-3-hydroxy-1,4-naphthoquinone, m.p. 102°–104.5° C.

EXAMPLE 10

Preparation of
3-Acetoxy-5-chloro-2-dodecyl-1,4-naphthoquinone

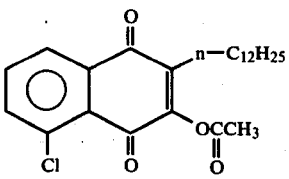

A solution of 0.95 parts of 5-chloro-2-dodecyl-3-hydroxy-1,4-naphthoquinone in 20 parts of anhydrous tetrahydrofuran was added under nitrogen to a mixture of 0.0635 parts of dispersed sodium hydride in 40 parts of tetrahydrofuran with stirring at room temperature. After 45 minutes of stirring, a solution of 0.275 parts of acetyl chloride in 30 parts of tetrahydrofuran was added and the mixture stirred for 5 hours. The tetrahydrofuran was stripped under reduced pressure and the residue taken up in methylene chloride and then washed with water, 10% hydrochloric acid, four more times with water, dried over sodium sulfate and stripped. The resulting yellow solid was purified by column chromatography on silica gel using 1-chlorobutane as eluent. Solvent removal gave 0.9 parts of 3-acetoxy-5-chloro-2-dodecyl-1,4-naphthoquinone, m.p. 57°–59° C.

By using the appropriate 2-alkyl-3-hydroxy-1,4-naphthoquinone and the appropriate acid chloride or anhydride, the following compounds shown in Table I could be similarly prepared by anyone skilled in the art, using the procedure outlined in Examples 1 through 10.

TABLE 1

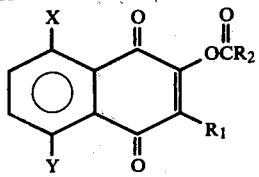

| $R_1$ | $R_2$ | X | Y | Melting Point (° C.) |
|---|---|---|---|---|
| -n-$C_8H_{17}$ | —$CH_2CH_2CH_3$ | Cl | H | — |
| -n-$C_8H_{17}$ | —$CH_3$ | $CH_3$ | H | — |
| -s-$C_8H_{17}$ | —$CH_3$ | Cl | Cl | — |
| —($CH_2$)$_4$—[S-cyclohexyl] | —$CH_3$ | Cl | H | — |
| -n-$C_{11}H_{23}$ | —$CH_3$ | Cl | H | — |
| -n-$C_{11}H_{23}$ | —$CH_2CH_2CH_3$ | Cl | $CH_3$ | — |
| -n-$C_{11}H_{23}$ | —$OCH_3$ | $OCH_3$ | H | — |
| -n-$C_{12}H_{25}$ | —$CH_2OCH_3$ | Br | H | — |
| -n-$C_{12}H_{25}$ | —$CH_3$ | Cl | $OCH_3$ | — |
| -n-$C_{12}H_{25}$ | —$CH_2OCH_2CH_3$ | H | Cl | — |
| -s-$C_{12}H_{25}$ | —CH(cyclopropyl) | Cl | Br | — |
| —($CH_2$)$_6$—[S-methylcyclopentyl] | —$OCH_3$ | Cl | H | — |
| -n-$C_{12}H_{25}$ | [S-cyclohexyl] | Br | H | — |
| -n-$C_{12}H_{25}$ | —($CH_2$)$_4CH_3$ | F | H | — |
| -n-$C_{12}H_{25}$ | —C($CH_3$)$_3$ | Cl | F | — |
| -n-$C_{13}H_{27}$ | —$OCH_2CH_3$ | $CH_3$ | $CH_3$ | — |
| -n-$C_{12}H_{25}$ | —O—CH($CH_3$)$CH_2CH_3$ | Cl | H | — |
| -n-$C_{12}H_{25}$ | —($CH_2$)$_{16}CH_3$ | Cl | H | — |
| -n-$C_{12}H_{25}$ | —CH=$CH_2$ | Br | $CH_3$ | — |
| -n-$C_{12}H_{25}$ | —CH=$CHCH_3$ | Br | F | — |
| -n-$C_{12}H_{25}$ | —C($CH_3$)=$CH_2$ | $OCH_3$ | Br | — |
| -n-$C_{12}H_{25}$ | —CH=$CHCO_2H$ | Cl | H | — |
| -n-$C_{12}H_{25}$ | —($CH_2$)$_7$CH=CH$CH_2$CH=CH($CH_2$)$_4CH_3$ | Cl | H | — |
| -n-$C_{12}H_{25}$ | —($CH_2$)$_7$CH=CH($CH_2$)$_7CH_3$ | Cl | H | — |
| -n-$C_{14}H_{29}$ | —$CH_3$ | $OCH_3$ | $OCH_3$ | — |
| -s-$C_{14}H_{29}$ | —$CH_2CH_3$ | H | $CH_3$ | — |
| —($CH_2$)$_8$—[S-cyclohexyl] | —CH=$CHCH_3$ | Cl | H | — |
| -n-$C_{10}H_{21}$ | —$CH_3$ | Cl | H | — |
| -n-$C_{12}H_{25}$ | —$CH_3$ | Br | Br | — |
| -n-$C_{12}H_{25}$ | —$CH_3$ | H | F | — |
| -n-$C_{12}H_{25}$ | —$CH_3$ | H | $OCH_3$ | — |
| -n-$C_{12}H_{25}$ | —$CH_3$ | H | Br | — |

TABLE 1-continued

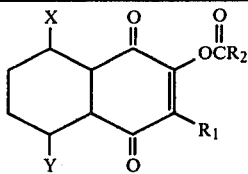

| R₁ | R₂ | X | Y | Melting Point (°C.) |
|---|---|---|---|---|
| -n-$C_{12}H_{25}$ | —$CH_3$ | Br | H | — |

Formulation and Use

The compounds of Formula I are useful as miticides and mite ovicides, and can be used to protect both plants and animals from damage caused by these pests. More specifically, fruits, field crops, vegetable, ornamentals, birds and other warm-blooded animals including man can also be protected.

When mites come into contact with the compounds of Formula I, either in the form of direct sprays or by walking over surfaces which have been treated, they rapidly become irritated and leave the area or are killed if they have been exposed to a sufficiently high dosage. While most plants or animals are able to tolerate the presence of very small numbers of mites without apparent adverse effect, large populations have been known to kill plants. Generally, as the weather becomes favorable, mite populations rapidly build up, easily outstripping parasite and predator capabilities for control. Growers noting rapid mite build-up must take immediate action to prevent damage to economically important crops. Thus, a method is needed for immediately reducing mite build-up and thereby preventing damage to important crops or animals.

The preferred method of this invention, namely, contacting mites and/or mite eggs with a miticidally and mite ovicidally effective concentration of one of the compounds of Formula I, is a most desirable method for control of these pests. For instance, very small quantities of compounds of Formula I are required for miticidal or mite ovicidal activity; additionally, the compounds are not rapidly washed from leaves by rain. They do not have any adverse effect on ladybird beetles, which are important mite predators, and the compounds rapidly degrade in the environment. The compounds are also effective against phosphorous-resistant strains of mites.

The quantity of compound needed for miticidal activity will vary depending on the specific situation. Among the variables that must be considered in deciding on the quantity of chemical to be used are the specific compound itself, the specific mite to be controlled, weather conditions, the type of crop, the stage of development of the crop, the volume of spray applied, population pressure, and the interval between applications. For plant protection, solutions or suspensions containing as little as 3.5 ppm of active ingredient in a spray solution may prove effective under a given set of circumstances. For field usage, however, in high-volume applications, aqueous spray preparations containing 30–4,000 ppm of active ingredient are generally useful. Preferred are suspensions containing 60–1,000 ppm, and most preferred are those containing 125–500 ppm. On an area basis, in general, 0.025 to 15 kilograms of active ingredient per hectare are acceptable, preferably 0.05 to 8 kilograms, and most preferably 0.08 to 4 kg. When applied in an orchard, spraying is continued until run-off is observed.

It may be desirable or useful to mix the compounds of this invention with other agricultural pesticides or adjuvants. Such mixtures often increase the effectiveness of the application on mites and broaden the scope of control to embrace other pests such as insects, fungi, nematodes, or bacteria. A mixture with a refined petroleum spray oil or superior oil may provide greater than additive results on mites. Other pesticides with which the compounds of this invention may be mixed to achieve broader-spectrum activity include:

diazinon—O,O-diethyl O-(2-isopropyl-4-methyl-6-pyrimidyl)phosphorothioate disulfoton—O,O-diethyl S-2-(ethylthio)ethylphosphorodithioate phorate—O,O-diethyl S-(ethylthio)methylphosphorodithioate oxamyl—S-methyl 1-(dimethylcarbamoyl)-N-[(methylcarbamoyl)oxy]trioformimidate methomyl—S-methyl N-(methylcarbamoyloxy)thioacetimidate benomyl—1-butylcarbamoyl-2-benzimidazolecarbamic acid, methyl ester captan—N-trichloromethylthiotetrahydrophthalimide maneb—ethylenebisdithiocarbamic acid, manganese salt carboxin—5,6-dihydro-2-methyl-1,4-oxathiin-3-carboxanilide streptomycin—2,4-diguanidino-3,5,6-trihydroxycyclohexyl-5-deoxy-2-o-(2-deoxy-2-methylamino-α-glycopyranosyl)-3-formylpentofuranoside The compounds are especially suited for the protection of living plants such as fruit-bearing trees, nut-bearing trees, ornamental trees, forest trees, vegetable crops, horticultural crops (including ornamentals, small fruit and berries) and grain and seed crops. Apple trees, peach trees, cotton, citrus trees, beans and peanuts are particularly susceptible to mite damage and can be protected by application of the compounds of this invention. To assure control throughout the "mite" growing season (e.g., June through September in the Northern Hemisphere) multiple applications at reasonably spaced intervals can be utilized.

Many species of mites are controlled by the compounds of this invention. The following is a list of representative susceptible mites along with the types of damage that they can cause: *Panonychus ulmi* (European red mite) and *Tetranychus urticae* (two-spotted mite) which are commonly called "orchard mites," and which attack a great many deciduous trees, such as apple, pear, cherry, plum and peach trees; *Tetranychus atlanticus*

(Atlantic or strawberry mite), *T. cinnabarinus* (carmine spider mite) and *T. pacificus* (Pacific mite); which attack cotton and numerous other crop plants; *Paratetranychus citri* (citrus red mite) and others which attack citrus; *Phyllocoptruta oleivora* which causes citrus rust; *Bryobia praetiosa* (clover mite) which attacks clover, alfalfa and other crops; and *Aceria neocynodomis* which attacks grasses and other plants.

Useful formulations of the compounds of Formula I can be prepared in conventional ways. They include solutions, emulsifiable concentrates, dusts, suspensions, emulsions, wettable powders, and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

|  | Percent by Weight | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Broks, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", McCutcheon Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

For further information regarding the art of formulation, see for example:

J. B. Buchanan, U.S. Pat. No. 3,576,834, April 27, 1971, Col. 5 Line 36 through Col. 7 Line 70 and Ex. 1–4, 17, 106, 123–140.

R. R. Shaffer, U.S. Pat. No. 3,560,616, Feb. 2, 1971, Col. 3 Line 48 through Col. 7 Line 26 and Examples 3–9, 11–18.

E. Somers, "Formulation", Chapter 6 in Torgeson, "Fungicides", Vol. I, Academic Press, New York, 1967.

Still another liquid formulation which is particularly convenient for small-scale use is the "aerosol" formulation which is packaged under pressure in a suitable container. The active ingredient may be present in a suspension, emulsion or solution. For simplicity in preparation and use, solutions are preferred. The pressure may be supplied by low-boiling liquids such as propane or chloro-fluoro carbons or by relatively soluble gases such as carbon dioxide or nitrous oxide.

EXAMPLE 11

| Emulsifiable Concentrate | |
| --- | --- |
| 3-Acetoxy-5-chloro-2-dodecyl-1,4-naphthoquinone | 25% |
| Blend of oil soluble sulfonates and polyoxyethylene ethers | 8% |
| Xylene + impurities in technical | 67% |

The ingredients are combined and stirred with gentle warming to speed solution. A fine screen filter is included in packaging operation to insure the absence of any extraneous undissolved material in the product.

EXAMPLE 12

| Emulsifiable Concentrate | |
| --- | --- |
| 3-Acetoxy-5,8-dichloro-2-dodecyl-1,4-naphthoquinone | 20% |
| Cyclohexanone | 50% |
| Aliphatic spray oil | 15% |
| Blend of polyoxyethylene ethers and oil soluble sulfonates | 15% |

The active ingredient is combined with cyclohexanone and emulsifiers, and the mixture is stirred and heated until solution is effected. Spray oil is then blended into the solution.

EXAMPLE 13

| Dust | |
| --- | --- |
| 3-Acetoxy-5-chloro-2-dodecyl-1,4-naphthoquinone | 5% |
| Attapulgite | 15% |
| Talc | 80% |

The active ingredient is blended with attapulgite and then passed through a hammer mill to produce particles substantially all below 200 microns. The ground concentrate is then blended with powdered talc until homogeneous.

EXAMPLE 14

| Emulsifiable Concentrate | |
| --- | --- |
| 3-Acetoxy-5-chloro-2-tetradecyl- | 20% |

| Emulsifiable Concentrate | |
|---|---|
| 1,4-naphthoquinone | |
| Chlorobenzene | 74% |
| Sorbitan monostearate and polyoxyethylene condensates thereof | 6% |

The ingredients are combined and stirred to produce a solution which can be emulsified in water for application.

Mite control for the compounds of Formula I is illustrated in the following examples.

EXAMPLE 15

Test units consisting of plant pots containing two red kidney beans in the 2-leaf stage were infested with 2-spotted mites and sprayed to run-off with dispersions of 3-acetoxy-5-chloro-2-dodecyl-1,4-naphthoquinone at various rates. Dispersions were made by dissolving an appropriately weighed quantity of the active ingredient in 10 ml of acetone and then diluting with water containing TREM 014 at 1:3000. Mortality was evaluated 2 days after spraying. A table of results is set forth below:

| Concentration of Active Ingredient (ppm) | % Mortality (24 hours) |
|---|---|
| 500 | 100 |
| 50 | 100 |
| 20 | 100 |
| 10 | 100 |
| 5 | 100 |
| 2.5 | 88 |

EXAMPLE 16

Red kidney bean plants in the 2-leaf stage were infested with mites which were allowed to oviposit. About 24 hours later the leaves were dipped in tetraethyl pyrophosphate solution to kill the mites. After drying, the plants were sprayed with test dispersions of 3-acetoxy-5-chloro-2-dodecyl-1,4-naphthoquinone at various rates. Dispersions were made by dissolving an appropriately weighed quantity of the active ingredient in 10 ml of acetone and then diluting with water containing TREM 014 at 1:3000. Hatching activity was observed and results were recorded five days later.

| Concentration of Active Ingredient (ppm) | % Ovicidal Activity (5 days) |
|---|---|
| 100 | 100 |
| 50 | 100 |
| 25 | 98 |
| 12.5 | 79 |
| Control (0) | 1 |

We claim:

1. A compound of the formula:

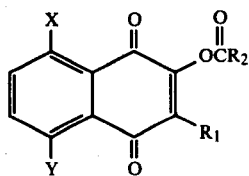

wherein
  $R_1$ is alkyl of 8–14 carbon atoms which are branched, cyclic or straight chain;
  $R_2$ is alkenyl of 2–17 carbon atoms;
  X is hydrogen, fluorine, chlorine, bromine, methyl or methoxy; and
  Y is hydrogen, fluorine, chlorine, bromine, methyl or methoxy;
provided that at least one of X and Y is other than hydrogen.

2. A compound of claim 1 wherein $R_1$ is an alkyl of 11–14 carbon atoms either branched or straight chain.

3. A compound of claim 1 wherein $R_2$ is alkenyl of 2 or 3 carbon atoms.

4. A compound of claim 1 wherein either X or Y is hydrogen.

5. A compound of claim 1 wherein $R_1$ is a straight chain alkyl of 11–14 carbon atoms.

6. A compound of claim 1 wherein $R_1$ is an alkyl of 11–14 carbon atoms either branched or straight chain; $R_2$ is alkenyl of 2 to 3 carbon atoms and either X or Y is hydrogen.

7. A compound of claim 6 wherein $R_1$ is a straight chain alkyl of 11–14 carbon atoms.

8. A method for protecting plants from mites or aphids which comprises applying to the plant a miticidally or aphicidally effective amount of a compound of claim 1.

9. A method for protecting plants from mites or aphids which comprises applying to the plant a miticidally or aphicidally effective amount of a compound of claim 2.

10. A method for protecting plants from mites or aphids which comprises applying to the plant a miticidally or aphicidally effective amount of a compound of claim 3.

11. A method for protecting plants from mites or aphids which comprises applying to the plant a miticidally or aphicidally effective amount of a compound of claim 4.

12. A method for protecting plants from mites or aphids which comprises applying to the plant a miticidally or aphicidally effective amount of a compound of claim 5.

13. A method for protecting plants from mites or aphids which comprises applying to the plant a miticidally or aphicidally effective amount of a compound of claim 6.

14. A method for protecting plants from mites or aphids which comprises applying to the plant a miticidally or aphicidally effective amount of a compound of claim 7.

15. A composition for the control of mites or aphids consisting essentially of a miticidally or aphicidally effective amount of a compound of claim 1 and at least one of (a) a surface-active agent and (b) a solid or liquid diluent.

16. A composition for the control of mites or aphids consisting essentially of a mitically or aphicidally effective amount of a compound of claim 2 and at least one of (a) a surface-active agent and (b) a solid or liquid diluent.

17. A composition for the control of mites or aphids consisting essentially of a mitically or aphicidally effective amount of a compound of claim 3 and at least one of (a) a surface-active agent and (b) a solid or liquid diluent.

18. A composition for the control of mites or aphids consisting essentially of a mitically or aphicidally effective amount of a compound of claim 4 and at least one of (a) a surface-active agent and (b) a solid or liquid diluent.

19. A composition for the control of mites or aphids consisting essentially of a mitically or aphicidally effective amount of a compound of claim 5 and at least one of (a) a surface-active agent and (b) a solid or liquid diluent.

20. A composition for the control of mites or aphids consisting essentially of a miticidally or aphicidally effective amount of a compound of claim 6 and at least one of (a) a surface-active agent and (b) a solid or liquid diluent.

21. A composition for the control of mites or aphids consisting essentially of a miticidally or aphicidally effective amount of a compound of claim 7 and at least one of (a) a surface-active agent and (b) a solid or liquid diluent.